(12) United States Patent
Asano et al.

(10) Patent No.: US 9,080,993 B2
(45) Date of Patent: Jul. 14, 2015

(54) MICRODEVICE, MICROCHIP APPARATUS AND ANALYSIS METHOD UTILIZING THE SAME

(75) Inventors: Naomi Asano, Osaka (JP); Yuichiro Shimizu, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 247 days.

(21) Appl. No.: 13/056,485

(22) PCT Filed: Jul. 28, 2009

(86) PCT No.: PCT/JP2009/063413
§ 371 (c)(1),
(2), (4) Date: Apr. 22, 2011

(87) PCT Pub. No.: WO2010/013704
PCT Pub. Date: Feb. 4, 2010

(65) Prior Publication Data
US 2011/0185827 A1 Aug. 4, 2011

(30) Foreign Application Priority Data
Jul. 29, 2008 (JP) ................................. 2008-195343

(51) Int. Cl.
*B01L 3/00* (2006.01)
*G01N 21/75* (2006.01)
*G01N 21/00* (2006.01)
(Continued)

(52) U.S. Cl.
CPC ...... *G01N 35/00069* (2013.01); *B01L 3/50273* (2013.01); *B01L 2300/0806* (2013.01); *B01L 2400/0409* (2013.01);
(Continued)

(58) Field of Classification Search
USPC ..................... 422/64, 68.1, 72, 82.05–82.09, 422/500–502
See application file for complete search history.

(56) References Cited

U.S. PATENT DOCUMENTS 5,061,381 A * 10/1991 Burd ............................ 210/789
6,063,589 A 5/2000 Kellogg et al.
(Continued)

FOREIGN PATENT DOCUMENTS

JP 2003-028883 1/2003
JP 2003-531018 10/2003
(Continued)

OTHER PUBLICATIONS

Cho, Seung-Jin et al., "Investigation of the Fundamental Measuring Techniques for Protein Sensing System," Sharp Technical Journal, vol. 94, pp. 46-51. Aug. 2006.

*Primary Examiner* — Jill Warden
*Assistant Examiner* — Julie Tavares
(74) *Attorney, Agent, or Firm* — Mintz Levin Cohn Ferris Glovsky and Popeo, P.C.; David G. Conlin; Steven M. Jensen

(57) ABSTRACT

Provided a microdevice capable of performing analysis quickly and at a high level of sensitivity even when a minute amount of sample solution is used. The microdevice is equipped with a rotation board, a reaction field provided on the rotation board, and an introduction portion for introducing a solution into the reaction field. The microdevice is characterized in that the following angle is always 45 to 90°: an angle of a part of a wall surface of the reaction field where the centrifugal force has the greatest effect with respect to the direction of the centrifugal force generated when the rotation board is rotated.

10 Claims, 18 Drawing Sheets

(51) Int. Cl.
*G01N 35/00* (2006.01)
*G01N 33/48* (2006.01)

(52) U.S. Cl.
CPC . *B01L 2400/0633* (2013.01); *B01L 2400/0672* (2013.01); *G01N 2035/00148* (2013.01)

(56) References Cited

U.S. PATENT DOCUMENTS

| | | | |
|---|---|---|---|
| 6,561,208 | B1 | 5/2003 | O'Connor et al. |
| 2003/0053934 | A1* | 3/2003 | Andersson et al. ............. 422/72 |
| 2005/0202733 | A1 | 9/2005 | Yoshimura et al. |
| 2009/0238724 | A1* | 9/2009 | Yamamoto et al. .......... 422/68.1 |
| 2011/0038758 | A1 | 2/2011 | Akaba et al. |

FOREIGN PATENT DOCUMENTS

| | | |
|---|---|---|
| JP | 2005-257337 | 9/2005 |
| JP | 2006-145451 | 6/2006 |
| JP | 2007-057378 | 3/2007 |
| WO | 2006/054689 | 5/2006 |
| WO | 2007/052648 | 5/2007 |
| WO | WO 2007052648 A1 * | 5/2007 |
| WO | WO 2008053150 A1 * | 5/2008 |

* cited by examiner (a)

(b)

(a) x-x' Cross Section (b) y-y' Cross Section (a)

(b) x-x' Cross Section (a)

(b)

(a) x-x' Cross Section (b) y-y' Cross Section (a)

(b)

(a) x-x' Cross Section (b) y-y' Cross Section (a)

(b)

(a) x-x' Cross Section (b) y-y' Cross Section (a)

(b)

(a) x-x' Cross Section (b) y-y' Cross Section (a)

(b)

(a)

(b)

(a)

(b)

(a)

(b)

(c)

(a)

(b) x-x' Cross Section

MICRODEVICE, MICROCHIP APPARATUS AND ANALYSIS METHOD UTILIZING THE SAME

FIELD OF THE INVENTION

The present invention relates to an analytical microdevice for detecting a test substance, i.e. a particular substance contained in a test solution (for example, allergens, adiponectins and cytokines), and to a method using the microdevice.

DESCRIPTION OF THE RELATED ART

Immune analysis utilizing antibody-antigen reaction is used as a significant means of analysis and measurement in fields including medical treatment, biochemistry, and allergen analysis. Conventional immune analysis, however, has posed problems including taking time for analysis, involving complicated handling, and so forth.

Under this situation, there has been developed a microtechnology applying microprocessing technology of semiconductors (Micro Electro-Mechanical System, MEMS). Thereby, in the biochemical analysis of proteins, genes and the like, a microtechnology using antigen-antibody reaction (Micro Total Analytical System, μ-TAS) is progressing rapidly.

For example, Patent Document 1 proposes a microdevice technology in which a micron-order channel (reaction field) is formed on a substrate, and antibodies or the like are immobilized on the microchannel, and thereby it becomes possible to shorten analysis time and to simplify an analysis operation.
[Patent Document 1]
Japanese Patent Application Publication No. 2007-57378

Patent document 1 relates to a technology of a microdevice having a protein immobilizing portion and antibodies immobilized on the surfaces thereof in a micro channel. This technique reduces the size of the reaction field (protein immobilizing portion) and enlarges the reaction surface area, thus realizing miniaturization of the device, simplifying the chip structure and significantly reducing the time required for reaction.

The structure of the microdevice according to the above-described technique is shown in FIG. 21, to which reference will be made in describing the technique in detail below. As shown in FIG. 21, the microdevice has a configuration in which a channel 101, a introduction portion 102, a damming portion 103 and a discharging portion 104 are provided on a substrate 100 formed of a translucent material such as glass or plastic. In addition, a protein immobilizing portion 105 is formed in the channel 101.

In the protein immobilizing portion 105, a microasperity 110, which is an asperity having a nanostructure as shown in FIG. 22, is formed on the inner wall of the channel. The thickness of the microasperity has ranges shorter than a wavelength of light emitted into the protein immobilizing portion for detection of a test substance. To the protein immobilizing portion, a protein that specifically reacts with a test substance is immobilized using well-known methods such as physical adsorption and a covalent bond with an amino group in the protein.

A detection method using this device is described with reference to FIG. 23. First, a solution containing a test substance 120 is mixed and reacted with a solution containing a labeled antibody 123 in which an optically detectable labeled substance 121 is bound to an antibody 122 bound to the test substance. Thereby, an immune complex 124 (a reaction product of the labeled antibody and the test substance) is formed.

Then, a mixture solution containing the immune complex 124 is introduced from an introduction portion 102 shown in FIG. 21 using an external pump and flowed through the channel. And then, as shown in FIG. 23, the immune complex 124 is reacted with an antibody 125 immobilized in a protein immobilizing portion 105 to form a complex 126 consisting of the antibody 125, the test substance 120 and the labeled antibody 123.

If necessary, a cleaning solution may be flowed in the channel for the purpose of removing an unreacted immune complex 124 and an unreacted labeled antibody 123.

Thereafter, light absorption, fluorescent emission, light emission and the like of the labeled substance 121 in the immune complex 124 bound to the protein immobilizing portion are detected using a given analytical instrument such as UV-visible spectroscopy, fluorescence analysis, chemiluminescence analysis and thermal lens analysis, depending on the kind of the labeled substance. Thereby, the amount of the test substance 120 in the test solution can be determined.

DISCLOSURE OF INVENTION

Problems to be Solved by the Invention

As a result of various studies on analytical devices with microchannels, the present inventors have founded the following problems.

(1) In a microdevices in which a protein immobilizing portion with a microasperity is formed on a surface of a channel, a reactive area can be increased. However, reaction of an antibody immobilized on the channel with a test substance (or a complex of a test substance and a labeled antibody) is affected by the distance between the antibody and the test substance, i.e. a diffusion distance required for the reaction of the test substance. Therefore, when the diffusion distance is large, the antibody immobilized to the channel can react with only the test substance near the antibody. Consequently, the result is obtained as if measuring a test substance solution thinner than actual concentration of the test substance. Therefore, the microdevice according to the prior art described above cannot perform trace analysis since the detection sensitivity cannot be sufficiently improved. As a countermeasure to this, it is considered to reduce the diffusion distance by narrowing the channel width or shallowing the channel depth. However, this method requires a complicated manufacturing process, and technical difficulty thus increases, leading to significantly increase production costs. As a result, this method is not practical.

(2) In addition, a method is known in which the solution flow is stopped to when the test substance reaches an antibody immobilizing area in order to increase an opportunity of reaction of a test substance (or a complex of a test substance and a labeled antibody) with an antibody immobilized on a surface of a channel. However, even in this method, when the distance between the test substance and the antibody immobilized on the channel is large (e.g. 50 nm or more), it takes time for the test substance to reach the antibody, and thus there is caused a problem of an increase in time required for the reaction.

The present invention has been made in view of the foregoing problems. It is an object of the present invention to provide an analytical microdevice which allows rapid microanalysis with high sensitivity.

Means for Solving the Problem

In order to solve the above problems, the present invention adopts a measure for rotating the microdevice and thereby decreasing a diffusion distance due to a generated centrifugal force.

The first invention of the microdevice to solve the above problems is characterized as follows. The microdevice comprises a rotation board, a reaction field provided on the rotation board, and an introduction portion for introducing a solution into the reaction field. And the following angle is always 45 to 90°: an angle formed between a direction of the centrifugal force generated when the rotation board is rotated and a tangent line at a part on the wall surface of the reaction field where the greatest centrifugal force is applied.

In this configuration, the part where the greatest centrifugal force is applied in the wall of the reaction field always has an angle of 45 to 90° with respect to the direction of the centrifugal force generated during the rotation of the rotation board (the direction of centrifugal force). Therefore, when a sample solution containing a target substance is introduced to the reaction field of the microdevices described above in a smaller volume than that of the reaction field and then the micro device is rotated, the sample solution is pressed against at least the part where the greatest centrifugal force is applied in the wall of the reaction field due to centrifugal force. This decreases the distance between the wall and the sample solution (diffusion distance). Thus, the reaction rate and sensitivity are exponentially increased, and the usage amount of the sample solution can be decreased. In a word, highly sensitive trace analysis is available.

The reaction field is an area where a reaction is performed, for example, such as immobilization reaction, antigen-antibody reaction and enzyme substrate reaction.

Here, the direction of centrifugal force means the direction of the centrifugal force caused by rotation of the rotation board, i.e. the direction represented by a group of numberless half lines (half lines occupying up to) 360°) extending from the center of rotation to the reaction field.

The rotation board may contain a hole at its center, as shown in FIG. 12.

The center of rotation is preset in the rotation board of the micro device. The center of rotation is generally located at the center of the rotation board. However, as shown in FIG. 19(*c*), the center of rotation may not be located at the center of the rotation board. In addition, there may be a virtual axis as the center of rotation at a hole provided in the rotation board.

A tangent line used in the present invention is defined as follows.

First, an intersection point is defines as a point where an arbitrary line of the above-mentioned group of numberless half lines intersects the inner wall on the far side from the center of rotation.

When the shape of the inner wall surface at the intersection is an arc (a curve), a tangent line is followed by a mathematical definition.

As shown in FIG. 19(*a*), when the shape of the inner wall surface at the intersection is a line, the line is defined as a tangent line.

When the shape of the inner wall surface at the intersection is a shape of a intersection of two lines, as shown in FIG. 19(*b*), a tangent line is a line perpendicular to a line extended from the center of rotation in the direction where the greatest centrifugal force is applied (the direction of the centrifugal direction).

As shown in FIG. 19(*c*), when a solution can flow in the reaction field in the direction of the centrifugal force, a tangent line is defined according to the above definitions depending on the shape of the wall intersecting a line extended in the direction of the centrifugal force.

Herein, "an angle with a tangent line is always 45 to 90°" means that the following angle is always 45 to 90°: an angle of a tangent line at a point (an intersection) where an arbitrary line of the above-mentioned group of numberless half lines intersects the inner surface of the wall on the far side from the center of rotation with respect to the arbitrary line.

In addition, "an area where the greatest centrifugal force is applied" exists on "the inner surface of the wall on the far side from the center of rotation". This inner surface of the wall is a wall surface along the direction in which a solution moves duo to the centrifugal force.

In the above configuration, a reactant may be immobilized at least in the part where the greatest centrifugal force is applied in the wall of the reaction field.

When a solution containing a substance that reacts specifically with a reactant is used as a sample solution, the above configuration can decrease a diffusion distance between a reactant and a solution containing a test substance.

In order to efficiently use a reactant and to efficiently react the reactant with a test substance, it is preferable to immobilize the reactant within a certain area centered on the part in the wall of the reaction field where the greatest centrifugal force is applied. This certain area is 75% or less, preferably 5% to 40% and more preferably 10% to 30% with respect to the total length of the cross section outline (the inner contour of the reaction field) in the case of cutting the reaction field in the direction perpendicular to the flow direction, centered on the part in the wall of the reaction field where the greatest centrifugal force is applied.

For example, when the cross section of the reaction field is rectangular, the reactant is immobilized only on the wall of the reaction field on the side of the centrifugal force direction, or on the three surfaces of the recess of the reaction field. However, of course, the reactant may be immobilized on the whole inner surface of the reaction field. The immobilization on the three surfaces of the recess or the whole inner surface of the reaction field has the disadvantage of increasing a usage of the reactant compared to others. On the other hand, it has the advantage of simplifying an operation for the immobilization. A solution containing a reactant may be flowed while rotating a microdevice to immobilize the reactant on the wall of the reaction field on the side of the centrifugal force direction.

In order to more effectively use the centrifugal force, the angle with the tangent line at the part where the greatest centrifugal force is applied is preferably 60 to 90°, more preferably 75 to 90°, and still more preferably 80 to 90°.

As the above reactant, there can be used known materials such as proteins (antibodies, etc.), peptides, amino acids and imprinted polymers.

In the above configuration, there may be further provided a detection portion for detecting an amount of the test substance, and a connection channel for connecting the reaction field and the detection portion.

In this configuration, since the detection may be performed in a different area from the reaction field, various detection methods can be used.

In the above configuration, the connection channel may be disposed substantially perpendicular to the plate surface of the rotation board.

In the case of adopting this configuration, since the detection portion can be placed in an area isolated from the reaction field where the reaction is carried out, the efficiency of detection is increased.

In the above case, in order to prevent the solution from flowing to the detection portion due to centrifugal force, it is preferable to set up a damming portion in the connection channel, or to locate the detection portion in the direction opposite to centrifugal force (at a more inner side than the reaction field).

In addition, the detection portion may be positioned farther from the center of rotation than the reaction field. In this case, it is preferable that the connection channel is formed substantially parallel to the direction of the centrifugal force. Moreover, in order to control a solution flow to the detection portion due to centrifugal force, it is preferable to form an on/off valve in the connection channel. Also, in order to control an outflow of the solution from the detection portion, it is preferable to form an on/off valve at the exit of the detection portion. In this configuration, the solution can be flowed into or out of the detection portion by an action of the on/off valve and the centrifugal force. Therefore, since a power source for pumping is not required, the device configuration can be simplified.

In terms of making centrifuge force more efficient, a planar shape of the reaction field against the rotation board is preferably a circumference or an arc centered on the center of rotation, or linear.

Moreover, it is preferable that a liquid reservoir portion for storing the sample solution (e.g. a test solution containing a test substance) is provided between the introduction portion and the reaction field so that the solution is flowed from the liquid reservoir potion to the reaction field when the centrifugal force is applied. In this configuration, if the test solution is injected before the rotation, since the solution flows into the reaction field as the rotation begins, excellent work efficiency can be obtained. In this configuration, it is more preferable to form an on/off valve between the liquid reservoir portion and the reaction field. In addition, there may be respectively provided a plurality of liquid reservoir portions for storing a solution containing a labeled test, a solution containing a substrate and the like.

In the above microdevice, the rotation board may be formed by laminating a group of plates including a main plate in which a groove for the reaction field is formed and a lid plate in which the introduction portion is formed.

Moreover, the rotation board may be formed by laminating a group of plates including a lid plate in which the introduction portion is formed, a main plate in which a groove for the reaction field and a through hole for the connection channel are formed, and a detection plate in which the detection portion is formed.

The microdevices having these structures are easy to fabricate.

The above-mentioned group of plates may include a plate other than those listed above, such as a plate in which an IC chip for detection is embedded. In addition, the main plate itself may include the detection portion, the connection channel and the like.

The second invention of a microchip apparatus to solve the above problems is characterized as follows. The microchip apparatus comprises a turntable and a microchip that is positioned with reference to a center of rotation of the turntable and fixed to the turntable. The microchip has at least a reaction field and an introduction portion for introducing a solution into the reaction field. In the condition where the microchip is fixed to the turntable, the following angle is always 45 to 90°: an angle formed between a direction of centrifugal force generated when the turntable is rotated and a tangent line at a part on the wall surface of the reaction field where the greatest centrifugal force is applied.

The second invention is different from the first invention in that a microchip in which the reaction field structure is created is separated from the turntable for applying centrifugal force to the microchip, and that the microchip is positioned based on the center of rotation of the turntable and fixed to a predetermined place in the turntable. All other matters are similar to the first invention. Therefore, the second invention can provide the same effect as the first invention. Furthermore, in the second invention, multiple of analyses can be performed simultaneously when multiple of microchips are placed on the turntable, and efficient analysis can be carried out by sequentially replacing the microchip.

As with the rotation board of the first invention, the turntable may have a hole at its center as shown in FIG. 17.

Herein, the first invention and the second invention are clearly discriminated by separating the terms "microdevice" and "microchip". However, in terms of a structure of the reaction field, the microdevice according to the first invention and the microchip according to the second invention have in common.

The center of rotation in the turntable is similar to that in the rotation board according to the first invention.

In the second configuration of the present invention, it is preferable to provide a mean to facilitate positioning and a fixing mean that does not move due to centrifugal force. Such means are not specifically limited, and known means can be widely used. For example, a system can be used in which a microchip is fitted to the plate surface. The following configuration can be also used: a fixed position of the microchip is marked, the microchip is placed at the fixed position and then fixed with a clip, a screw, a rubber band or the like.

In the structure of the second invention, the microchip may further comprise a detection portion for detecting an amount of the test substance, and the connection channel connecting the reaction field and the detection portion. The effect of this configuration is similar to that of the first invention.

In the structure of the second invention, the planar shape of the reaction field against the rotation board is preferably linear.

In the second invention in which a small microchip is placed, it is sometimes difficult to set the planar shape of the reaction field to an arc or a circumference centered on the center of rotation, while it is easy to set it to a linear shape.

In the second invention, as with the first invention, a liquid reservoir portion for temporarily storing a solution containing a test substance may be provided between the introduction portion and the reaction field. The same applies to the on/off valves.

In the first or second invention, the wall of the reaction field may be subjected to water repellent treatment.

It is preferable to subject the surface of the reaction field to water-repellent treatment because the solution dispersed on the wall of the reaction field is instantly aggregated to form droplets. The droplets can be easily moved (transported) by flowing air or nitrogen gas through the reaction field.

The third invention of an analytical method using the above-mentioned various micro devices and microchip apparatuses is characterized as follows. The method comprises: an introduction step for introducing a solution containing a target substance into the microdevices or the microchip; and a rotation step of rotating the microdevice. And the introduction amount of the solution containing a target substance is less than a volume of the reaction field.

According to the method described above, when the microdevices or microchip is rotated in the rotation step, the solution containing a target substance is pressed against the wall of the reaction field in the direction of centrifugal force. Thereby, since the diffusion distance is decreased between the solution containing a target substance and the wall of the reaction field where the greatest centrifugal force is applied, a reaction rate and detection sensitivity are exponentially improved, and the reaction can be surely performed even in the case of a small amount of solution containing a target substance. Thus, a trace analysis becomes available.

In this analysis method, the introduction amount of the solution containing a target substance is less than a volume of the reaction field. However, for example, it is preferable that an introduction amount of the solution containing a target substance is such an amount that the test solution is thinly spread (e.g. a thickness of 10 μm to 50 μm) on the wall of the reaction field due to the centrifugal force.

If a desired solution amount is predetermined in relation to the target substance, the introduced amount and the sizes of the reaction field, the channel and the detection portion are adjusted depending on the test substance. However, when a protein or the like is immobilized on the wall of the reaction field, the solution is not necessary to be spread over the entire wall surface of the reaction field, and, of course, the amount of solution only has to be such an amount that the solution is thinly spread on a part of the wall of the reaction field.

When the amount of solution is such an amount that the solution is to thinly spread on a part of the wall of the reaction field, or when a reactant is immobilized on only a part of the wall of the reaction field, it is preferable to use a pre-mixed solution of a test substance and a labeled antibody (a complex formed by reacting the test substance with the labeled antibody) as a solution containing a target substance. The reason is as follows. In the case of that an introduced solution amount or a reaction area is limited, when the test substance and the labeled antibody are introduced separately, some of the solution containing the labeled antibody does not come down to a site where there exists a complex of the immobilized reactant and the test substance, and thus there may be a risk that the reaction is insufficiently performed.

The fourth invention of an analytical method is characterized as follows. The method comprises: a fixing step for positioning a microchip relative to the center of rotation of a turntable, and then fixing the microchip to the turntable, the microchip having at least a reaction field and an introduction portion for introducing a solution containing a target substance into the reaction field; an introduction step for introducing the solution containing a target substance from the introduction portion; and a rotation step of rotating the turntable after the introduction step. The fixing step is a step for positioning and fixing the microchip so that the following angle is always 45 to 90°: an angle formed between a direction of the centrifugal force generated when the turntable is rotated and a tangent line at a part on the wall surface of the reaction field where the greatest centrifugal force is applied. In addition, the analytical method is characterized in that an introduction amount of the solution containing a target substance is smaller than a volume of the reaction field.

This analysis method provides the same effect as the above third invention.

Effect of The Invention

As described above, the present invention can provide a microdevice and an apparatus that allow analysis of a trace amount of sample solution, high sensitivity to the target substance, and very quick and accurate analysis.

BRIEF DESCRIPTION OF DRAWINGS

[3] FIG. 3(a) is a top view, and FIG. 3(b) is a sectional view along x-x' of FIG. 3(a).

[16] FIG. 16(a) shows the microchip apparatus, and FIG. 16(b) shows the microchip.

[17] FIG. 17(a) shows the microchip apparatus, and FIG. 17(b) shows the microchip.

Figure 20:
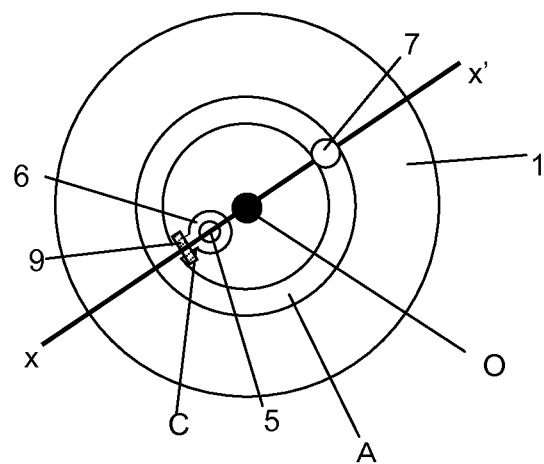
Figure 20:
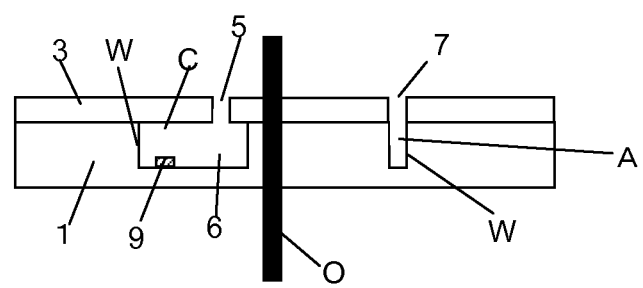

[20] FIG. 20 (a) is a top view of the microdevice according to Example 1, and FIG. 20 (b) is a sectional view along the x-x' line of the microdevice according to the Example.

Figure 21:
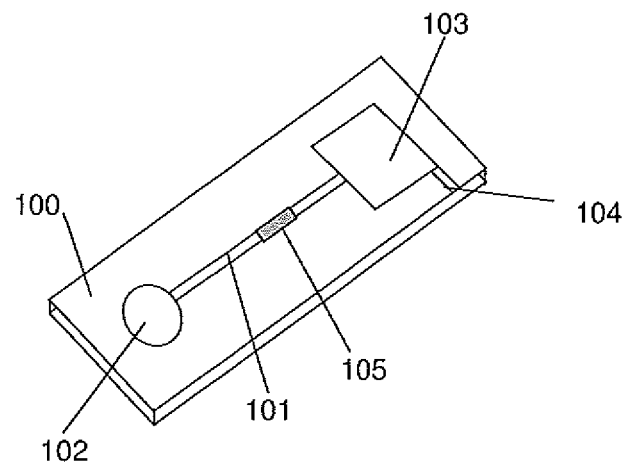

[21] FIG. 21 shows a top view showing a conventional microdevice.

Figure 22:
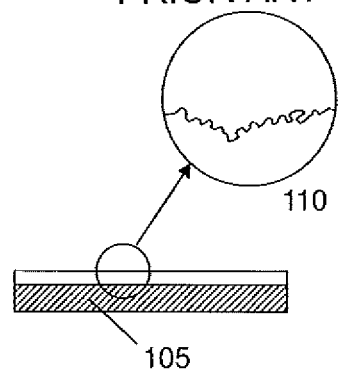

[22] FIG. 22 is an enlarged view of a reaction part of a conventional microdevice.

Figure 23:
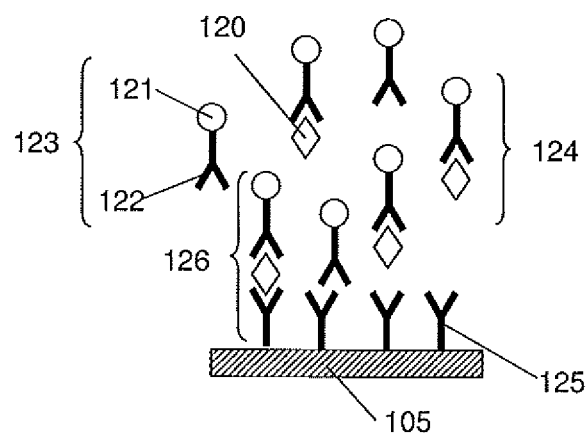

[23] FIG. 23 shows a schematic diagram of reaction in a reactive part of a conventional microdevice.

BEST MODE FOR CARRYING OUT THE INVENTION

Hereinafter, embodiments of the microdevice according to the present invention will be described in detail using the drawings.

[Embodiment 1-1]

Figure 1:
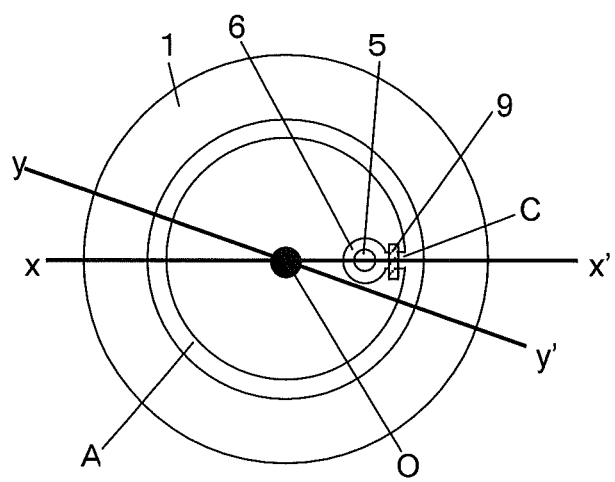
FIG. 1(a) is a top view of the rotation board of the micro device according to Embodiment 1-1.
FIG. 1(b) is a top view of the detection plate of the micro device according to Embodiment 1-1.
Figure 1:
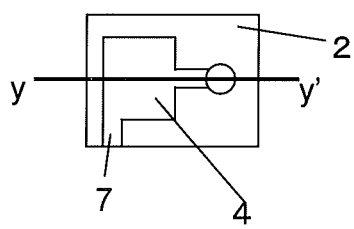
Figure 2:
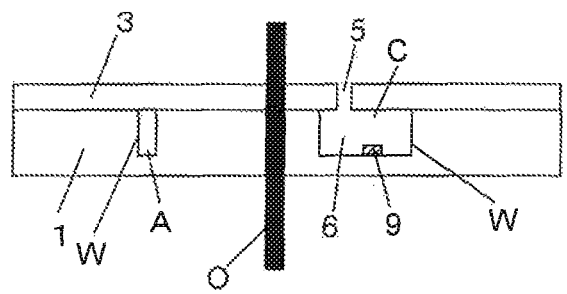
FIG. 2(a) is a sectional view along the x-x' line of the microdevice according to Embodiment 1-1.
FIG. 2(b) is a sectional view along the y-y' line of the microdevice according to Embodiment 1-1.
Figure 2:
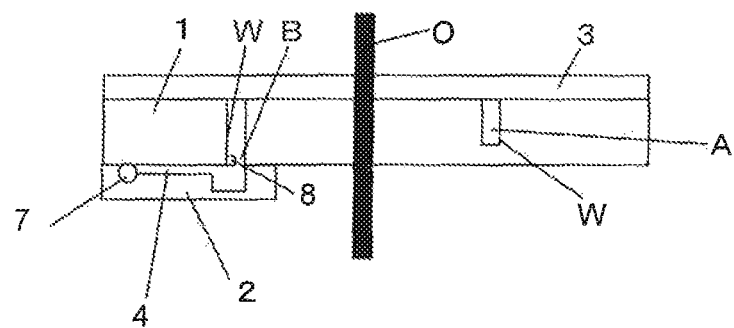

FIG. 1 is a schematic top view showing the structure of the microdevice according to this embodiment, and FIG. 2 shows a longitudinal sectional view along the x-x' and y-y' lines of the micro device according to this embodiment.

This microdevice has a configuration in which, as shown in FIG. 2(b), there is laminated a group of plates composed of a main plate 1 having an approximately circular shape in a plan view as shown in FIG. 1(a), a detection plate 2 having an approximately rectangular shape in a plan view as shown in FIG. 1(b), and a lid plate 3 as shown in FIG. 2 (a).

As shown in FIGS. 1 and 2, this microdevice comprises: a reaction field A in which a reactive substance (e.g. an antibody protein) specifically linked to a test substance is immobilized; a detection portion 4; and a connection channel B that connects the reaction field A and the detection portion 4. The microdevice further comprises: an introduction portion 5 for introducing a test solution or a buffer solution (e.g. phosphate buffer) into the device; a liquid reservoir portion 6 for retaining a certain amount of the test solution; and a channel C connecting the liquid reservoir portion 6 and the reaction field A. In addition, a discharge portion 7 for discharging a test solution or a buffer solution to the outside of the device is formed at the downstream end of the detection portion 4.

On the main plate 1, grooves for the reaction field A, the liquid reservoir portion 6 and the channel C, and a through hole for the connection channel B are formed, respectively. A planar shape of the main plate is, but not limited to, preferably circular or elliptical. And it is preferred that the thickness of the main plate 1 is about 0.1 to 5 mm.

The rotation board is formed of the main plate 1, the detection plate 2 and the lid plate 3.

The reaction field A has about 1 μm to 1 mm width and about 1 μm to 1 mm depth. The cross section of the reaction field A is not particularly limited. As long as a test solution and a buffer solution are flowable therein, the cross section may be arbitrarily selected from circular, elliptical, semicircular or rectangular. A plane shape of the reaction field in this embodiment is a circumference centered on the center of rotation O. Thus, the angle between the centrifugal force direction and the part where the greatest centrifugal force is applied in the wall of the reaction field (the angle with tangent at the part where centrifugal force is applied) is always 90°.

The connection channel B is a connection between the reaction field A and the detection portion 4, and connects a bottom of the reaction field A with a lower surface of the main plate 1 (perpendicularly to the surface of the main plate). In addition, a projection 8 is formed on the wall on the side of the centrifugal force direction of the connection channel B. This projection 8 serves as a damming portion that prevents a test solution from being discharged along the wall of the connection channel B to the detection portion 4 due to the centrifugal force generated during the rotation of the device. Even if the detection portion 4 is located more downward in the gravity direction than the reaction field A, when a centrifugal force greater than the gravity is applied, the solution does not flow to the detection portion 4. A cross section of the connection channel B is not particularly limited. As long as a test solution and a buffer solution are flowable therein, the cross section may be arbitrarily selected from circular, elliptical, semicircular, rectangular, etc. Its size is set to about 1 μm diameter or more.

The liquid reservoir portion 6 is a portion for introducing a certain amount of a test solution, a buffer solution or the like into the microdevice. A planar shape of the liquid reservoir portion 6 is not limited, and may be circular, elliptical, polygonal, or any others.

The channel C is a connection between the reaction field A and the liquid reservoir portion 6. An on/off microvalve 9 is formed in the channel C so as to prevent a test solution from flowing out to the reaction field A before reaction. The cross section of the channel C is not particularly limited. As long as a test solution and a buffer solution are flowable therein, the cross section may be arbitrarily selected from circular, elliptical, semicircular, rectangular, etc. Its size is about fpm or more.

As the on/off microvalve 9, any valve may be used, but it is preferable to use a valve using electrowetting technology because of its simplicity. In this case, a wall of the channel C is made hydrophobic in advance to such a degree that a fluid does not flow out due to centrifugal force caused by rotation. When it is intended to flow a solution, voltage is applied to be hydrophilic and to release the flow blockage.

As shown in FIG. 1(b), the detection portion 4 and the discharge portion 7 are formed on the detection plate 2. The shape of the detection plate 2 is not limited. And the thickness of the detection plate 2 is preferably about 0.1 mm to 5 mm.

The detection portion 4 is a portion for detection. For example, in the case of the detection using a UV-visible spectrophotometer, a fluorometer and a thermal lens spectrophotometer that are installed outside of the device, a certain means does not have to be formed in the detection portion. However, it is preferable not to form a thing that interrupts the detection (for example, a thing that may block light). Furthermore, when electrochemical detection is performed, electrodes are provided in this portion. The shape and size of the detection portion are not particularly limited.

The discharge portion 7 is formed at the downstream end of the detection portion 4. The discharge portion 7 is provided to discharge the test solution, a buffer solution or the like out of the microdevice, which opens to the lateral face of the detection plate 2. The shape of discharge portion 7 is not particularly limited, and may have a circular, elliptical, polygonal or any other shape. Its cross sectional width is set to about or more.

As shown in FIG. 2 (a), the introduction portion 5 is formed on the lid plate 3. The shape of the lid plate 3 is not particularly limited. Its thickness is preferably about 0.1 mm to 5 mm.

The introduction portion 5 is a portion through which the test solution or a buffer solution is introduced into the microdevice. The planar shape of the introduction portion 5 is not limited, and may have a circular, elliptical, polygonal or any other shape. Its cross-sectional width is about 1 μm or more.

The surfaces of the reaction field A, the connection channel B, channel C, the introduction portion 5, liquid reservoir portion 6 and the discharge portion 7 may be subjected to water repellent treatment. If they are not subjected to water-repellent treatment, when the rotation is stopped, the solution remains splashed on the wall of the channel and the reaction field. Meanwhile, if they are subjected to water-repellent treatment, the solution splashed on the wall of the channel and the reaction field is instantly aggregated to form liquid drops. Since the liquid drops are easily transferred when air or nitrogen gas is flowed through the channel and the reaction field, transfer time of the solution is preferably shortened.

Glass, quartz, silica, ceramics, polymer materials and the like can be used as a material of the main plate 1.

Also, glass, quartz, silica, ceramics, polymer materials and the like can be used as a material of the detection plate 2, When an optical detection is performed, a transparent material having resistance against damage due to bending or the like is preferable.

Moreover, glass, quartz, silica, ceramics, polymer materials and the like can be also used as a material of the lid plate 3.

The method for producing parts such as a channel in the main plate 1, the detection plate 2 and the lid plate 3 is not particularly limited. A mechanical process such as micro-drilling or a chemical treatment such as etching may be used. Otherwise, a photothermosetting resin or a thermosetting resin is flowed into a mold with a pattern of the channel to form them as an integral structure. Also, for example, plate materials including polyolefin resins, polymethacrylate resins and polycarbonate resins may be formed by hot embossing technique using a mold with a pattern of the channel.

When the surfaces of the reaction field A, the connection channel B, the channel C, the introduction portion 5, the liquid reservoir portion 6 and the discharge portion 7 are subjected to water-repellent treatment, a known method may be employed such as coating with a hydrophobic polymer and chemical modification using a toluene solution of octadodecyltrichlorosilane. In addition, water-repellent materials (e.g. PTFE (polytetrafluoroethylena may be used as a plate.

Various reactants (e.g. proteins) can be immobilized in the reaction field A. Typically, there is immobilized an antibody that specifically reacts with a test substance. When a protein such as an antibody is immobilized in the reaction field A, there may be adopted a well-known immobilization method such as physical adsorption, covalent bond of functional groups on the surface of the reaction field A with amino groups of proteins, and an intake (inclusive) of proteins by a polymer having a three-dimensional network structure.

The immobilized location of the protein that specifically reacts with the test substance is at least a wall on the side of the direction of centrifugal force (the inner wall farther from the center of rotation, denoted by reference symbol "W" in FIGS. 2(a)-(b), 3(b), 5(a)-(b), 7(a)-(b), 9(a)-(b), 11(a)-(b), 13, and 17(b)) among walls of the reaction field. However, at least this area only has to be used as an immobilizing site, and therefore it is not excluded to immobilize it on the entire wall of the reaction field.

In order to immobilize a reactant on the wall on the side of the direction of centrifugal force, for example, a solution containing the reactant (e.g. an antibody) is introduced into the reaction field, and centrifugal force is applied so as to stick the solution on the wall. When this state continues, the reactant is adsorbed and fixed to the wall surface. If a solution containing an antibody is filled and adsorbed in the reaction field without attaching a lid plate, the antibody can be immobilized on the entire surface of the groove.

Analysis using this microdevice is described below.

When the microdevice is filled with a buffer solution or the like, the solution is pushed out or sucked out by means of a pump or the like to be removed.

(Introduction Step)

A solution containing a test substance (test solution) is introduced into the microdevice through an introduction portion 5. For the introduction of the test solution, the solution is pushed by an external pump connected to the introducing portion 5, or sucked out by an external pump connected to a discharge portion 7. For example, after a tube or the like is attached to the introduction portion 5, a syringe pump may be used. In this case, the test solution introduced through the introduction portion 5 stays in a liquid reservoir portion 6 by an on/off microvalve 9.

Preferably, in order to prevent nonspecific adsorption of proteins to the surfaces of the reaction field A, the connection channel B, the channel C and the detection portion 4, an albumin solution is flowed before the introduction of a test solution to form an albumin membrane (a nonspecific adsorption prevention membrane), and then a buffer solution is flowed for washing. In particular, it is desirable to form the nonspecific adsorption prevention membrane on the surface of the detection portion.

(Rotation Step)

After the liquid reservoir portion 6 is filled with the test solution, the microdevice is rotated. At this point, when a gate of the on/off valve is made hydrophilic due to voltage application so that the liquid can go through, centrifugal force transfers the test solution from the liquid reservoir portion 6 to the reaction field A.

Figure 18:
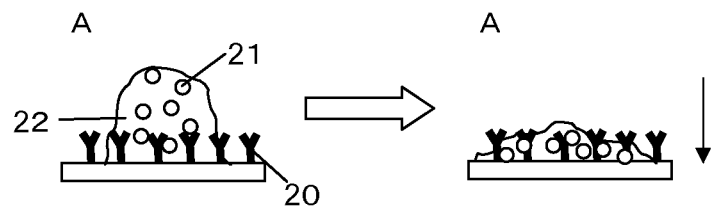
FIG. 18 is a schematic diagram showing liquid behavior in the microdevice according to Embodiment 1-1. The arrow in this figure shows the direction of centrifugal force.
Figure 19:
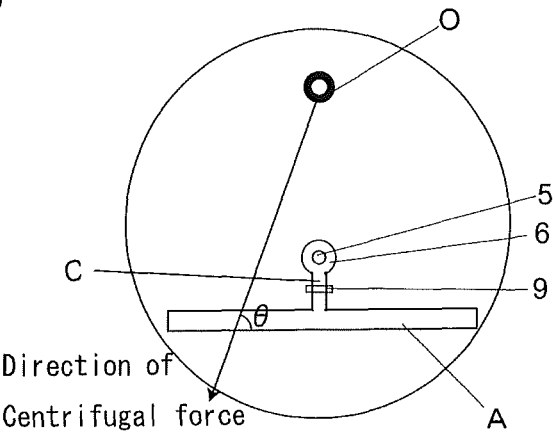
FIG. 19 shows a diagram illustrating an angle with respect to the tangent line of the reaction field in the microdevice according to the present invention.
Figure 19:
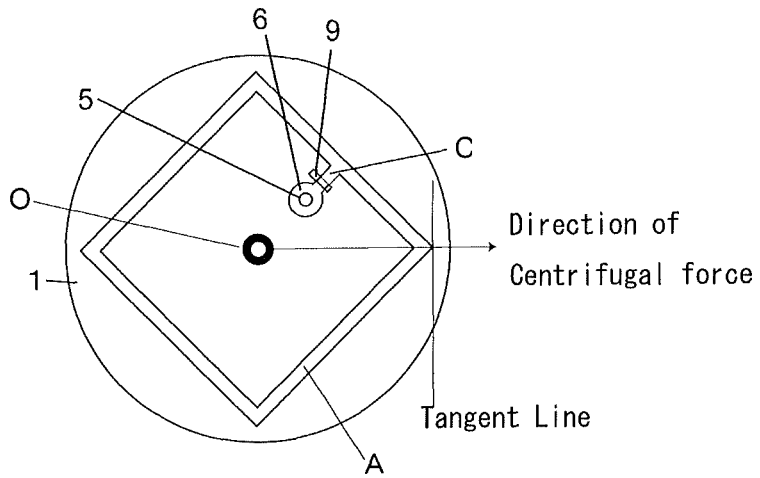
Figure 19:
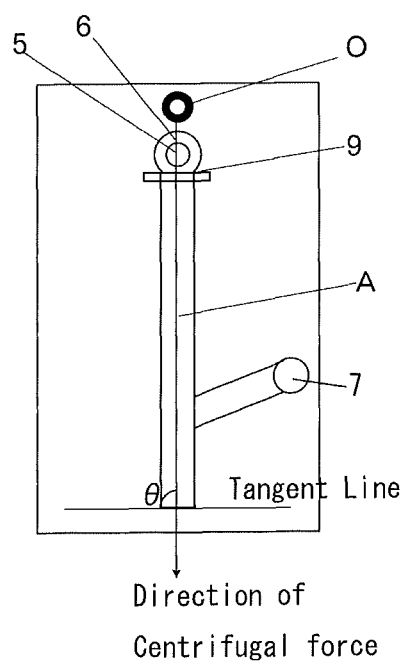

Thereby, a test substance contained in the test solution specifically reacts with a protein immobilized in the reaction field A to form an immobilized antibody-test substance complex. As shown in FIG. 18, since the test solution introduced from the introduction portion 5 is thinly spread on the outside wall of the reaction field A due to centrifugal force of the rotation, a diffusion distance between the test substance and the immobilized antibody is shortened, and thus the reaction time is decreased.

Then, the rotation of the micro device is stopped, and the test solution is discharged to the outside of the device by sending air or nitrogen from the introduction portion 5. At this time, if the channel wall and the reaction field wall have been treated with water-repellent, since the test solution is automatically aggregated to form liquid drops, the transport by air and so on becomes easy and the time required for the liquid discharge can be reduced.

Thereafter, a buffer solution is introduced into the microdevices to perform washing.

Next, while the microdevice is rotated, a solution containing a labeled antibody is introduced from the introduction portion. The labeled antibody specifically reacts with the test substance to form an immobilized antibody-test substance-labeled antibody complex. As mentioned above, since the solution containing the labeled antibody introduced from the introduction portion 5 is thinly spread on the outside wall of the reaction field A (on which a reactant is immobilized) due to centrifugal force of the rotation, a diffusion distance between the test substance and the labeled antibody is shortened, and thus the reaction time is decreased.

The labeled antibody has a configuration in which a labeling substance suitable for a used detection method is bound to an antibody that specifically reacts with the test substance. As the labeling substance, for example, enzymes and the like are used. As long as an antibody used as the labeled antibody has an antigen recognition site that is different from that of the antibody immobilized in the reaction field A, a polyclonal antibody or a monoclonal antibody may be used.

Thereafter, the rotation of the micro device is stopped, and the labeled antibody solution is discharged to the outside of the device by sending air or nitrogen from the introduction portion 5.

The solution containing the test substance and the solution containing the labeled antibody may be premixed, reacted, and then introduced in the introduction portion, or may be introduced separately as described above.

When an antibody is immobilized on entire or partial walls of the reaction field and a solution is introduced in such an amount that the solution is thinly sticked on a part of the wall of the reaction field, or when an antibody is immobilized on only the wall on side of the direction of centrifugal force, it is preferable to use a complex of the test substance and the labeled antibody as an introduced test solution. The reason is as follows. When a labeled antibody and a test substance are introduced separately, a solution containing the labeled antibody may not be properly distributed to an area where there exist a complex of the test substance and the antibody immobilized on the reaction field, and thereby there is a risk that the reaction becomes insufficient.

A buffer solution is further introduced to perform washing.

Next, while the microdevice is rotated, a substrate solution for an enzyme in the labeled antibody is introduced from the introduction portion. The substrate reacts with the enzyme to form a detectable substance. The effect of centrifugal force as described before allows to shorten the reaction time.

Thereafter, the rotation of the micro device is stopped, and the solution obtained after the enzyme substratereaction is transferred to the detection portion by sending air or nitrogen from the introduction portion 5.

Thereafter, the amount of the formed detectable substance is detected by a suitable detection method. The detection method includes absorbance measurement using a thermal lens or a UV-visible spectrophotometer, and electrochemical detection.

Figure 3:
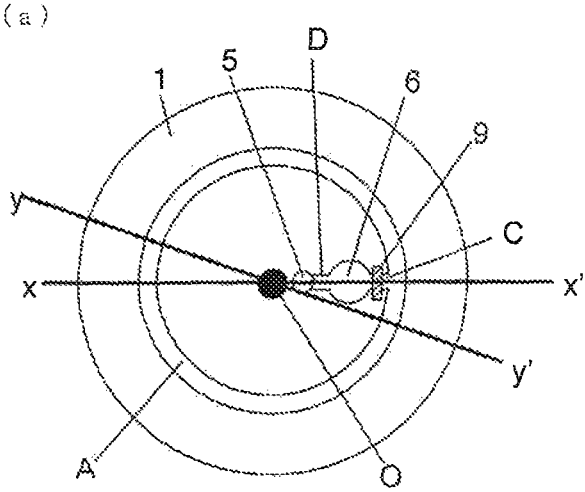
FIG. 3 shows a modified example of the location of the introduction portion according to Embodiment 1-1, where
Figure 3:
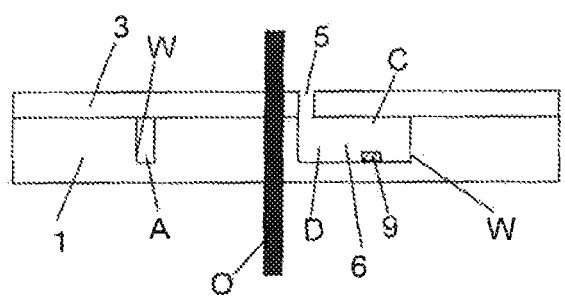

The introduction position 5 does not have to be provided above the liquid reservoir portion 6. For example, as shown in FIG. 3, the introduction position 5 may be provided at a position closer to the center of rotation (the direction opposite to the centrifugal force) than the liquid reservoir portion 6.

[Embodiment 1-2]

Figure 4:
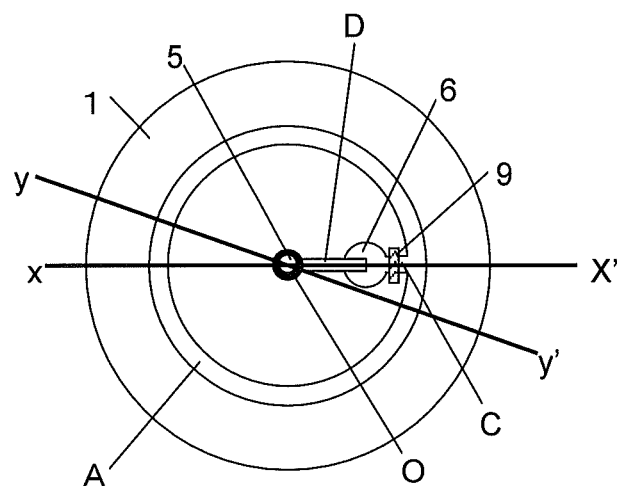
FIG. 4(a) is a top view of the rotation board of the microdevice according to Embodiment 1-2.
FIG. 4(b) is a top view of the detection plate of the microdevice according to Embodiment 1-2.
Figure 4:
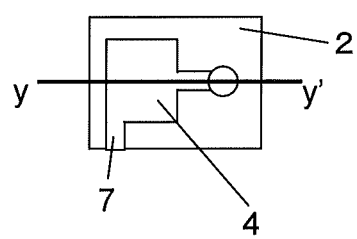
Figure 5:
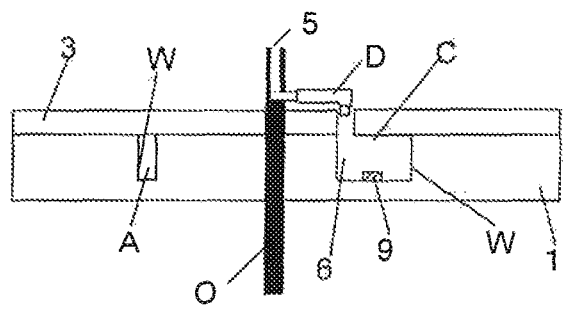
FIG. 5(a) is a sectional view along the x-x' line of the microdevice according to Embodiment 1-2.
FIG. 5(b) is a sectional view along the y-y' line of the microdevice according to Embodiment 1-2.
Figure 5:
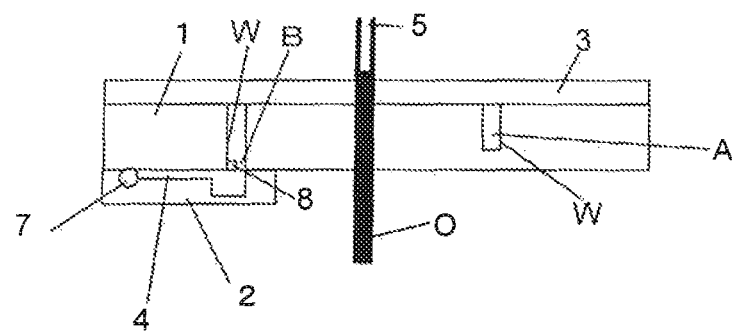

FIG. 4 is a top view showing a schematic structure of the microdevice according to the present invention. And FIG. 5 is a longitudinal sectional view along the x-x' and y-y' lines of the microdevice according to this Embodiment. This Embodiment is similar to above Example 1-1 except that an introduction portion 5 is provided above the center of rotation O but not on the main plate 1 and that a channel D connecting the introduction portion 5 and a liquid reservoir portion 6 is provided. In this structure, since the introduction portion 5 stays at the same place even during the rotation, the sample can be easily introduced into the microdevice during the rotation.

The shape of the channel D is not particularly limited. As long as a test solution and a buffer solution are flowable therein, the shape may be arbitrarily selected from circular, elliptical, semicircular, rectangular, etc. Its diameter is about 1 µm or more. In addition, the material of the channel D may be selected from any materials.

The surface of the channel D may be subjected to water-repellent treatment. With the water-repellent treatment, the solution splashed on the wall of the channel and the reaction field is instantly aggregated to form liquid drops. Since the liquid drops are easily transferred by a flow of air or nitrogen gas through the channel and the reaction field, transfer time of the solution is preferably shortened.

In this micro device, a test solution is introduced from the introduction portion 5 of the microdevice shown in FIG. 4(*a*) or 5(*a*). The test solution may be introduced into the microdevice during rotation, but it is not necessary to rotate the microdevice in advance. For the introduction of a test solution, either the solution is pushed by an external pump connected to the introduction portion 5, or aspirated by an external pump connected to the discharge portion 7. For example, a tube or the like is connected to the introduction portion 5 and then a syringe may be used. When a test solution is introduced without rotation, the solution is introduced into the liquid reservoir portion 6 by an external pump or air, and then the microdevice is rotated. Others are the same as Embodiment 1-1.

[Embodiment 1-3]

Figure 6:
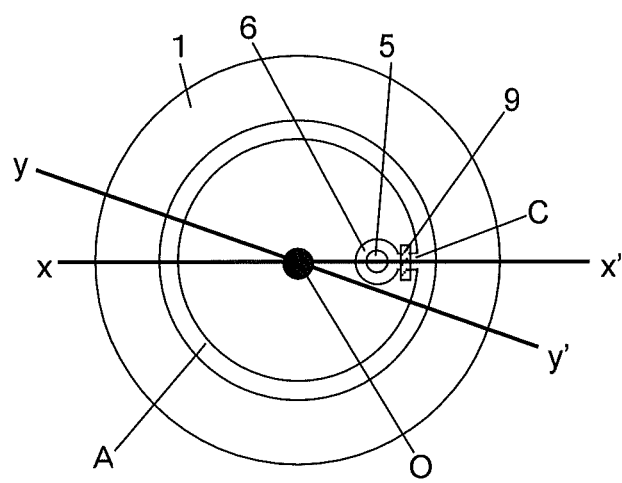
FIG. 6(a) is a top view of the rotation board of the micro device according to the Embodiment 1-3.
FIG. 6(b) is a top view of the detection plate of the micro device according to Embodiment 1-3.
Figure 6:
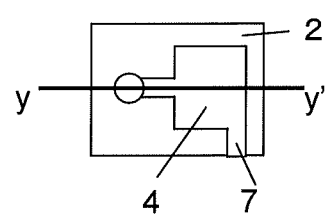
Figure 7:
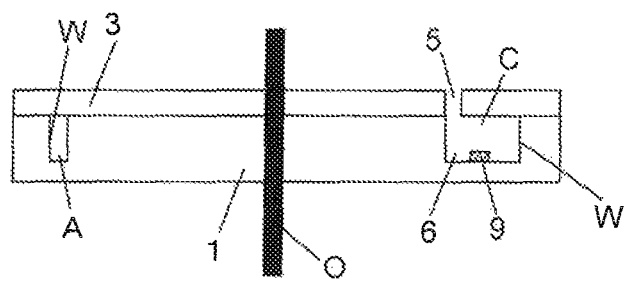
FIG. 7(a) is a sectional view along the x-x' line of the microdevice according to Embodiment 1-3.
FIG. 7(b) is a sectional view along the y-y' line of the microdevice according to Embodiment 1-3.
Figure 7:
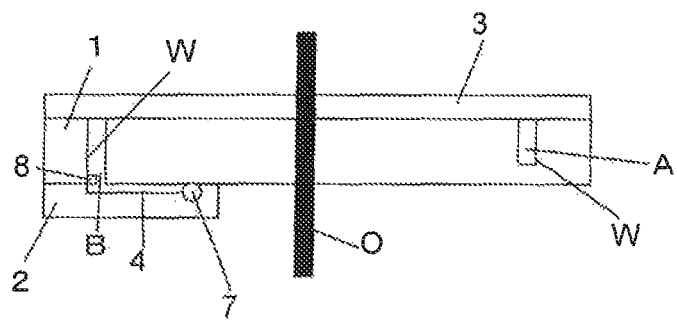

FIG. 6 is a top view showing a schematic structure of the microdevice according to the present invention. And FIG. 7 is a longitudinal sectional view along the x-x' and y-y' lines of the microdevice according to Embodiment 1-3. In Embodiment 1-3, the positional relationship between the reaction field A and the detection portion is opposite to that in Embodiment 1-1 relative to the direction toward the center of rotation. In this structure, as shown in FIG. 7 (*b*), since both the detection portion 4 and the discharge portions 7 are arranged closer to the center of rotation than the reaction field A, a solution cannot be discharged from the discharge portion 7 due to centrifugal force of the rotation even without a dammed portion.

An analysis method using this microdevice is similar to that in Embodiment 1-1. However, as described above, this structure provides advantages that it is not needed to provide a dammed portion because a solution cannot be discharged due to centrifugal force of the rotation.

[Embodiment 1-4]

Figure 8:
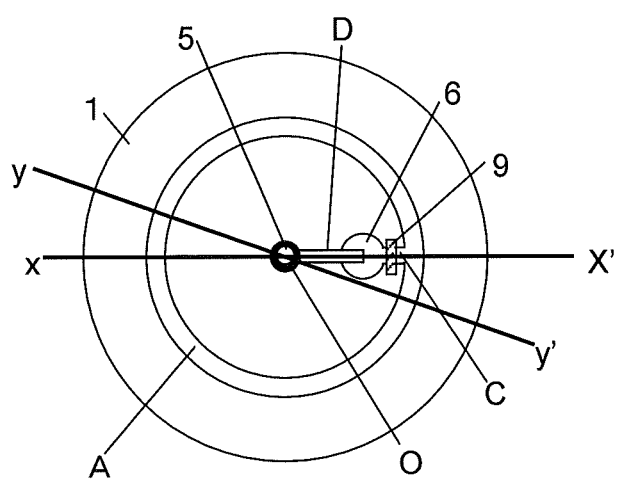
FIG. 8(a) is a top view of the rotation board of the micro device according to the embodiment 1-4.
FIG. 8(b) is a top view of the detection plate of the micro device according to Embodiment 1-4.
Figure 8:
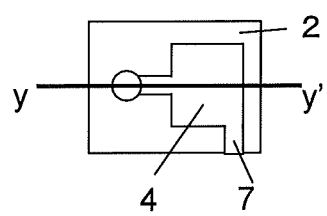
Figure 9:
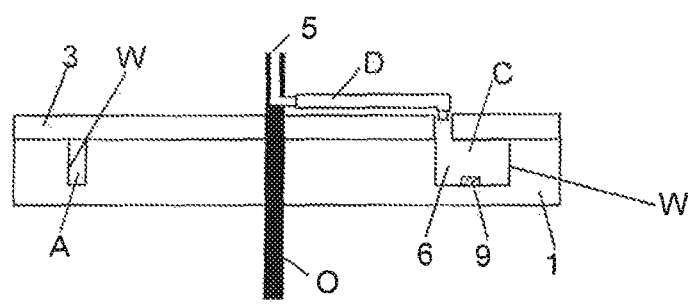
FIG. 9(a) is a sectional view along the x-x' line of the micro device according to Embodiment 1-4.
FIG. 9(b) is a sectional view along the y-y' line of the microdevice according to Embodiment 1-4.
Figure 9:
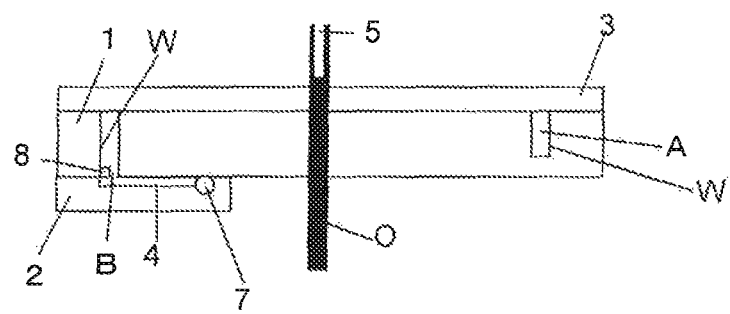

FIG. 8 is a top view showing a schematic structure of the microdevice according to Embodiment 1-4. And FIG. 9 is a longitudinal sectional view along the x-x' and y-y' lines of the microdevice according to Embodiment 1-4. Embodiment 1-4 is a combination of Embodiment 1-2 and Embodiment 1-3. This structure provides advantages that it becomes easy to introduce a sample to the plate during rotating and the solution cannot be discharged from the discharge portion 7 during the rotation.

[Embodiment 1-5]

Figure 10:
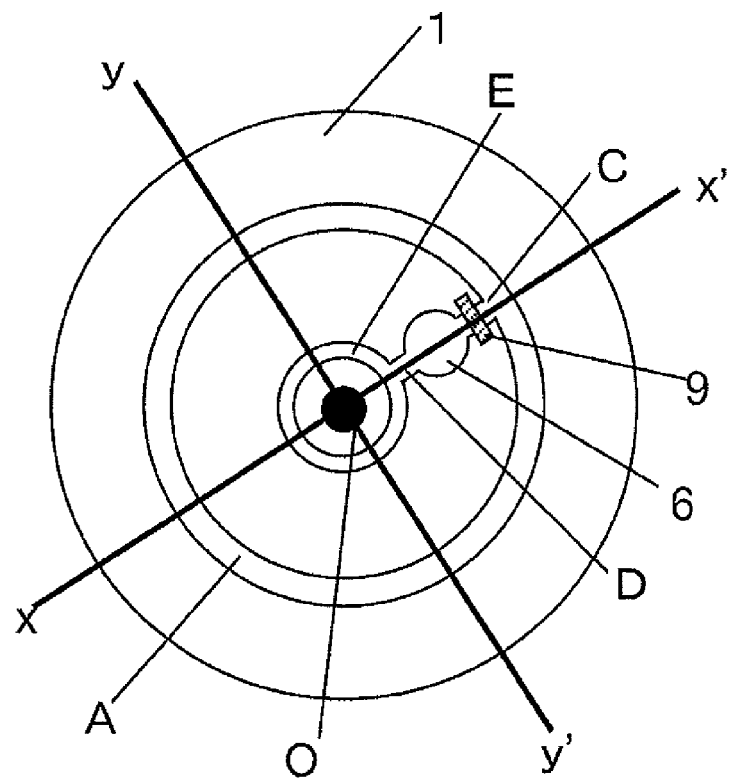
FIG. 10(a) is a top view of the rotation board of the microdevice according to Embodiment 1-5.
FIG. 10(b) is a top view of the detection plate of the microdevice according to Embodiment 1-5.
Figure 10:
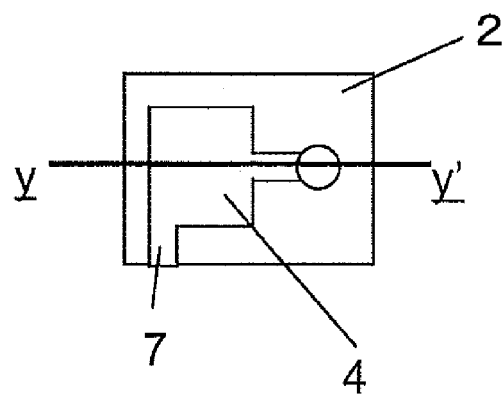
Figure 11:
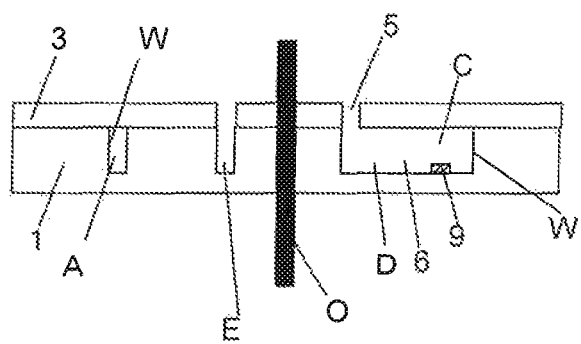
FIG. 11(a) is a sectional view along the x-x' line of the microdevice according to Embodiment 1-5.
FIG. 11(b) is a sectional view along the y-y' line of the microdevice according to Embodiment 1-5.
Figure 11:
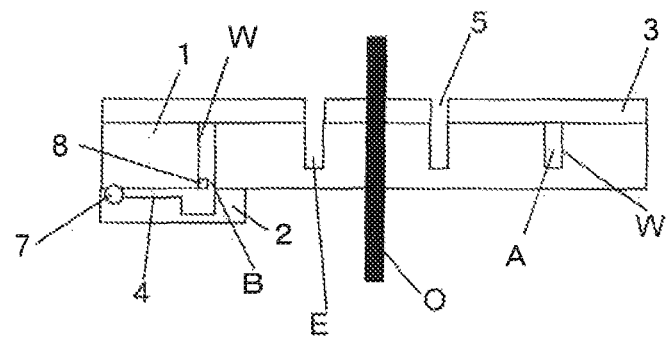

FIG. 10 is a top view showing a schematic structure of the microdevice according to Embodiment 1-5. And FIG. 11 is a longitudinal sectional view along the x-x' and y-y' lines of the microdevice according to Embodiment 1-5. Embodiment 1-5 is similar to Embodiment 1-1 except that a channel E, serving as an introduction portion, and a channel D, connecting the channel E and the liquid reservoir portion 6, are formed on the inner side of the reaction field A. In this structure, since whole of the channel E serves as an introduction portion, a sample can be easily introduced into the plate during rotation.

As shown in FIGS. 11(*a*) and (*b*), the channel E is open to the upper surface of the main plate 1. The cross section of the channel E is not particularly limited. As long as a test solution, a buffer solution and the like are flowable therein, the cross section may be arbitrarily selected from circular, elliptical, semicircular, rectangular, etc. Its size is set to about 1 µm diameter or more.

As shown in FIG. 10(*a*), the channel D is a connection between the channel E and the liquid reservoir portion 6. The cross section of the channel D is not particularly limited, As long as a test solution, a buffer solution and the like are flowable therein, the cross section may be arbitrarily selected from circular, elliptical, semicircular, rectangular, etc. Its size is set to about 1 μm or more.

The channels D and E may be subjected to water repellent treatment. When they are subjected to water-repellent treatment, the solution splashed on the wall of the channel and the reaction field is instantly aggregated to form liquid drops. Since the liquid drops are easily transferred by a flow of air or nitrogen gas through the channel and the reaction field, transfer time of the solution is preferably shortened.

In this microdevice, a test solution is introduced into the channel E shown in FIG. 10(a) as an introduction portion while the microdevice is rotated. The test solution may be directly introduced into the channel E with a syringe or the like. At first, the introduced test solution is thinly spread on the side where the centrifugal force is applied in the channel E due to the centrifugal force, but then the solution gradually moves through a channel D to a liquid reservoir portion 6. When the liquid reservoir portion 6 is filled with the solution, an on/off microvalve is opened and thereby the solution is flowed to the reaction field A in which an antibody or the like is immobilized due to the centrifugal force. Thus, there is no need to connect an external pump, etc, Subsequent operations are similar to above Embodiment 1-1.

Also in Embodiment 1-5, as with Embodiments 1-3 and 1-4, the position of the detection portion 4 may be changed. In the structure shown in FIG. 10, as in Embodiment 1-3, the detection portion is provided closer to the center of rotation than the reaction field A. Thus, there is no possibility that the solution is discharged from the discharge portion 7 due to centrifugal force.

[Embodiment 1-6]

Figure 12:
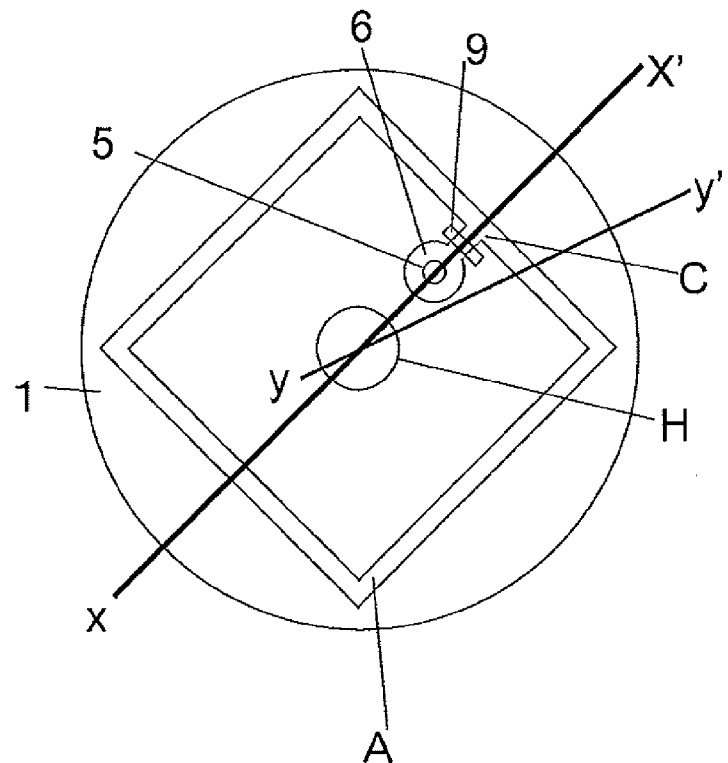
FIG. 12 shows the microdevice according to Embodiment 1-6, and (a) is a top view and (b) is a sectional view along the x-x' line of (a).
Figure 12:
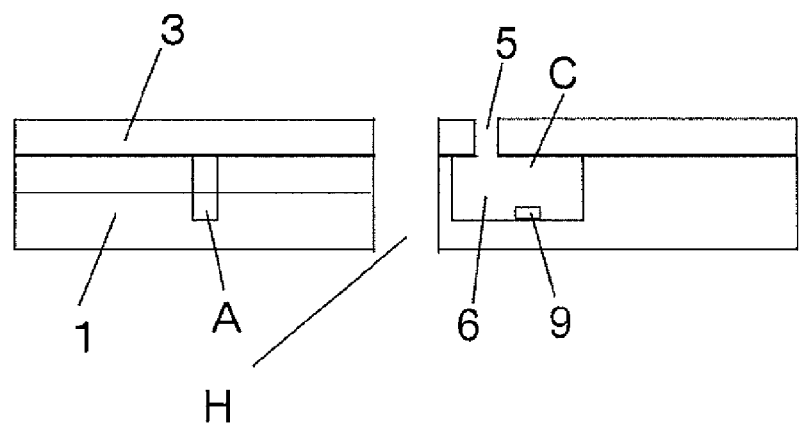

FIG. 12 is a diagram showing a schematic structure of the microdevice according to Embodiment 1-6. FIG. 12(a) is its top view. FIG. 12(b) is its longitudinal sectional view along the x-x' line. Embodiment 1-6 is similar to Embodiment 1-1 described above except that a hole H is provided in the center of the main plate (a virtual axis as a center of rotation is located at this hole H.) and that a planar shape of the reaction field A is a polygon (a square in the figure). Thus, even when the configuration of the plates and channels of the microdevices is changed in the above way, the same effect as that in Embodiment 1-1 can be obtained.

[Embodiment 2]

Figure 13:
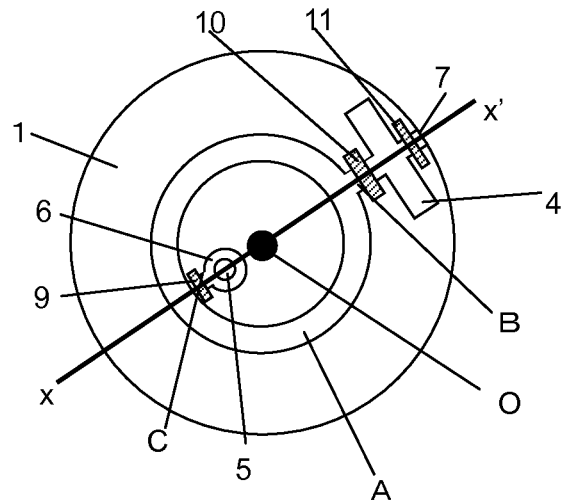
FIG. 13 is a top view of the rotation board of the microdevice according to Embodiment 2.
Figure 14:
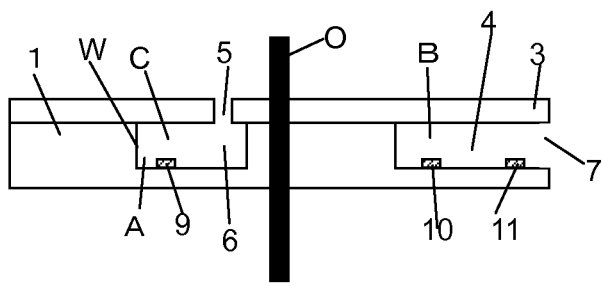
FIG. 14 is a sectional view along the x-x' line of the microdevice according to Embodiment 2.

FIG. 13 is a top view showing a schematic structure of the microdevice according to Embodiment 2. FIG. 14 is a longitudinal sectional view of a micro device according to this embodiment. In Embodiment 2, a detection portion 4 is provided in the main plate 1, a connection channel B is substantially parallel to the direction of centrifugal force, and on/off microvalves 10 and 11 are formed on the connection channel B and in front of a discharge portion, respectively. With this structure, there is no need to separate the main plate from the detection plate as described in above Embodiment 1. Thus, the rotation board is composed of the main plate 1 and a lid plate 3.

The on/off microvalves 10 and 11 shown in FIG. 13 are formed of a gold electrode, etc. The on/off microvalves 10 and 11 are adjusted to hydrophobic in advance so that a solution does not flow due to the centrifugal force of rotation. When it is intended to flow the solution, voltage is applied to make the valves hydrophilic.

In the microdevice according to Embodiment 2, a premixture of a test solution and a labeled antibody is introduced from an introduction portion 5 and then transferred to a liquid reservoir portion 6.

After the test solution is filled in the liquid reservoir portion 6, an electric current is flowed to the on/off micro valve 9 to open the valve. Thereby, the test solution is sent to the reaction field A due to the centrifugal force by rotation, and is thinly spread on a wall of the reaction field where the greatest centrifugal force is applied. Since a reactant such as an antibody is immobilized at least on the above-mentioned wall, a target substance in the test solution reacts with the reactant. Thereafter, an electric current is flowed to the on/off micro valve 10 to discharge the solution from a discharge portion 7. Other matters are similar to those in above Embodiment 1-1.

When the on/off micro valve 10 is for one use only, it is necessary to premix the test solution and the labeled antibody, but if not, they may be introduced sequentially.

Also in Embodiment 2, it is possible to dispose the introduction portion closer to the center of rotation than the liquid reservoir portion 6 as shown in FIG. 3, to provide an introduction portion at the center of rotation as in Embodiment 1-2, and to create a channel E that serves as an introduction portion as in Embodiment 1-3.

These structures provide similar effects to those in Embodiment 1-2 and Embodiment 1-3.

[Embodiment 3]

Figure 15:
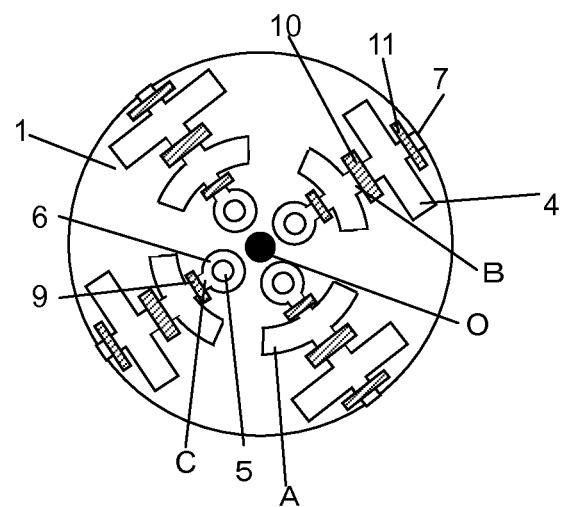
FIG. 15 shows a top view of the micro device according to Embodiment 3.

FIG. 15 is a top view showing a schematic structure of a microdevice according to the present invention. This structure allows to perform multiple measurements or reactions simultaneously.

This microdevice is equipped with a plural of introduction portions 5, liquid reservoir portions 6, reaction fields A, connection channels B, channels C, detection portions 4, discharge portions 7, and on/off microvalves 9,10 and 11.

The usage of this microdevice is similar to that in Embodiment 2, but there is an advantage that multiple measurements or reactions can be performed using one device at one time.

[Embodiment 4-1]

The microchip apparatus according to Embodiment 4-1 is characterized in that a microchip smaller than a rotatable turntable is placed on the turntable. That is, in the microchip apparatus of Embodiment 4-1, a turntable for rotating a microchip is separated from the microchip with a channel system including elements such as a reaction field, an introduction portion, a liquid reservoir portion and a reactant, and one or more microchips are placed and fixed at a predetermined position on the turntable.

The microchip as a major component of this apparatus may be almost the same as the microdevices described in above Embodiments 1-1 to 1-6, 2, and 3 except that the center of rotation is not provided. And the structure of the channel system may be quite similar.

In the microchip apparatus according to Embodiment 4-1 in which the turntable is separated from the microchips forming the channel system, multiple microchips can be disposed on the turntable, and thus a number of reactions and measurements can be performed at one time. In addition, since the microchips on the turntable can be replaced, there is an advantage that analysis can be performed continuously.

Figure 16:
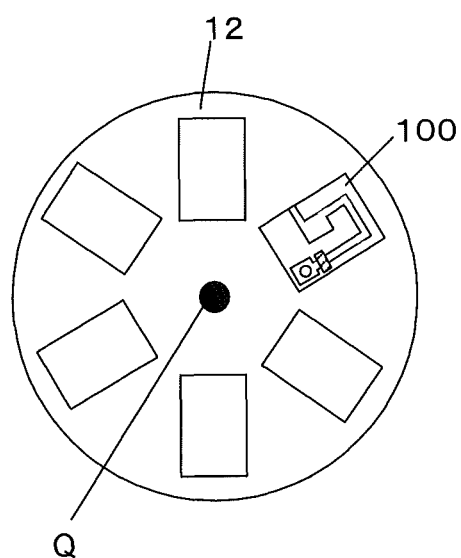
FIG. 16 is a top view of the microchip apparatus according to Embodiment 4-1, where
Figure 16:
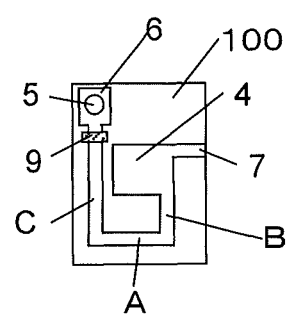

FIG. 16 is a top view showing a schematic structure of a microchip apparatus according to Embodiment 4-1. In the microchip apparatus shown in FIG. 16(a), six recesses which are slightly smaller than the dimension of the microchip are formed at evenly divided positions on the turntable 12 having the center of rotation Q, and each of the microchips is fitted in one of the recesses.

However, a fixing method of the microchip is not limited to the above fitting method. As a fixing method, it is preferred that the replacement of the chip is easy and the fix is kept even during rotation. For example, after a fixing position is marked, the microchip may be placed at the marked position and fixed with a clip, a screw, an elastic member such as a rubber band, etc. The number of the microchips placed on the turntable is not limited to six. One or more chips are preferred. In addition, a size, shape and material of the turntable 12 are not particularly limited. A rotation speed of the turntable 12 only has to be set appropriately.

The microchip apparatus of Embodiment 4-1 is further explained. as shown in FIG. 16(*b*), this apparatus comprises, on a microchip 100, an introduction portion 5 for introducing a test solution and a buffer solution, a liquid reservoir portion 6 for weighing a certain amount of the test solution, a reaction field A in which a protein that specifically binds to a test substances is immobilized, a channel C connecting the liquid reservoir portion 6 and the reaction field A, a detection portion 4 in which detection is performed, a connection channel B connecting the reaction field A and the detection portion 4, and a discharge portion 7. The shape of the channel plate 100 is not particularly limited, and its preferred thickness is 0.1 mm to 5 mm.

The reaction field A is approximately set to a width of 1 μm to 1 mm and a depth of 1 μm to 1 mm. The cross section of its channel is not particularly limited. As long as a test solution and a buffer solution are flowable therein, the cross section may be arbitrarily selected from circular, elliptical, semicircular, rectangular, etc. The plane shape of the reaction field is a line segment here. And when placed on the turntable, the reaction field is designed so that the angle with the direction of the centrifugal force is within a defined range.

The connection channel B connects the reaction field A and the detection portion 4. The cross section of the connection channel B is not particularly limited. As long as a test solution and a buffer solution are flowable therein, the cross section may be arbitrarily selected from circular, elliptical, semicircular, rectangular, etc. Its size is set to about 1 μm diameter or more.

The introduction portion 5 is a through hole formed in the lid plate overlapped with a channel plate, and is provided so as to introduce a test solution or a buffer solution into the microchip. The planar shape of the introduction portion 5 is not particularly limited, and may be circular, elliptical, polygonal, or any others. The width of the cross section is set to about 1 μm diameter or more.

The liquid reservoir portion 6 is a portion for introducing a certain amount of a test solution, a buffer solution or the like into the microdevice. The planar shape of the liquid reservoir portion 6 is not limited, and may be circular, elliptical, polygonal, or any others.

The channel C is a connection between the liquid reservoir portion 6 and the reaction field A. The cross section of the channel C is not particularly limited. As long as a test solution and a buffer solution are flowable therein, the cross section may be arbitrarily selected from circular, elliptical, semicircular, rectangular, etc. Its size is about 1 μm diameter or more.

The detection portion 4 is a portion in which detection is performed. For example, in the case of detection using a UV-visible spectrophotometer, a fluorometer and a thermal lens spectrophotometer that are installed outside of the device, a certain means does not have to be formed in the detection portion. However, it is preferable not to form a thing that interrupts the detection. Furthermore, when electrochemical detection is performed, electrodes are provided in this portion. The shape and size of the detection portion are not particularly limited.

The discharge portion 7 is provided to discharge the test solution, a buffer solution or the like out of the microdevice, and opens to the side surface of the channel plate. The shape of discharge portion 7 is not particularly limited, and may have a circular, elliptical, polygonal or any other shape. Its cross sectional width is set to about 1 μm diameter or more.

The surfaces of the reaction field A, the connection channel B, channel C, the introduction portion 5, liquid reservoir portion 6 and the discharge portion 7 may be subjected to water repellent treatment. If they are not subjected to water-repellent treatment, when the rotation is stopped, the solution remains splashed on the wall of the channel and the reaction field. Meanwhile, if they are subjected to water-repellent treatment, the solution splashed on the wall of the channel and the reaction field is instantly aggregated to form liquid drops. Since the liquid drops are easily transferred by flowing air or nitrogen gas through the channel and the reaction field, transfer time of the solution is preferably shortened.

In order to fix an antibody on the wall positioned on the side of the centrifugal force direction, for example, the chip is stood up with the wall down (the direction of gravity), and then a solution containing an antibody is introduced to the reaction field to adsorb and immobilize the antibody on the wall. Otherwise, a solution containing an antibody is filled in the reaction field without a lid plate, and adsorbed to immobilize the antibody on the whole surface of the groove.

An analysis method using this microchip apparatus is described below.

A test solution is introduced from an introduction portion 5 shown in FIG. 16(*b*). For the introduction of the test solution, the solution is pushed using an external pump connected to the introducing portion 5, or is aspirated using an external pump connected to a discharge portion 7. For example, a tube or the like is connected to the introduction portion 5, and then a syringe may be used. And the microchip is preferably declined so as not to discharge the introduced test solution from an outlet of the discharge portion.

Preferably, in order to prevent a nonspecific adsorption of proteins to the surfaces of the reaction field A, the connection channel B, the channel C and the detection portion 4, it is preferable that an albumin aqueous solution is flowed before the introduction of test solution to form an albumin membrane (a nonspecific adsorption prevention layer) and then washing is performed with a buffer solution. Especially, it is important to form a nonspecific adsorption prevention layer on the surface of the detection portion.

As shown in FIG. 16(*a*), the microchip to which a test solution is introduced is positioned and fixed in the turntable 12 so that the following angle is always 45 to 90°: an angle formed between the direction of the centrifugal force generated when the turntable is rotated and a tangent line at a part on the wall surface of the reaction field where the greatest centrifugal force is applied. (In this embodiment, the angle with the tangent line is 90° in the middle of the reaction site A.)

Thereafter, the turntable is rotated. A test substance contained in the test solution specifically reacts with a protein immobilized in the reaction field A to form an immobilized antibody-test substance complex. As shown in FIG. 18, the test solution, which has been introduced from the introduction section 5 and accumulated in the liquid reservoir portion, is thinly spread on the outside inner wall of the reaction field A due to the centrifugal force by the rotation, and thus the diffusion distance between the test substance and the immobilized antibody is decreased to shorten the reaction time.

The subsequent operations are similar to Embodiment 1-1.

[Embodiment 4-2]

Figure 17:
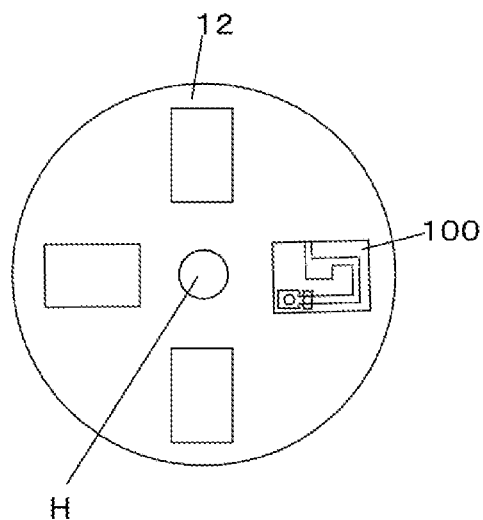
FIG. 17 is a top view of the microchip apparatus according to Embodiment 4-2, where
Figure 17:
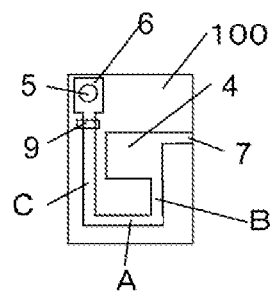

FIG. 17 shows a microchip apparatus according to Embodiment 4-2. The microchip apparatus according to Embodiment 4-2 is similar to that according to above Embodiment 4-1 except that a hole H is provided at the center of the rotatable turntable (A virtual axis as a center of rotation is located in this hole H). In this configuration, the effects similar to Embodiment 4-1 can be also obtained.

EXAMPLES

Example 1

This Example corresponds to Embodiment 1-1. As shown in FIG. 20, a reaction field A, which is circumferential in plan view, having a width of 400 μm and a depth of 50 μm was formed on a planar circular plate 1 (main plate) having a diameter of 4 cm and a thickness of 1 mm. In addition, an introduction portion 5 and a discharge position 7 were formed at the position corresponding to the overlapped area with the reaction field A in the main plate 1, in a 0.5 mm thick acrylic plate (lid plate 3). Then, these were laminated as shown in FIG. 20(b) to complete a microdevice.

In this Example, among the four walls constituting the reaction field, antibodies were immobilized on three surfaces except the top surface. In addition, since the planar shape of the reaction field was a circumference centered on the center of rotation O, the angle between the reaction field and the direction of centrifugal force was 90°.

While the microdevice was rotated, a solution containing anti-cryj-1 antibody was flowed to the reaction field A of the microdevice, and thereby the anti-cryj-1 antibody was immobilized in the reaction field A. Cryj-1 is an allergen contained in cedar pollens.

Albumin aqueous solution was flowed in the microdevice to form an albumin membrane (nonspecific adsorption prevention membrane) on the wall of the reaction field, and then washing was performed with a buffer solution.

Cryj-1 was dissolved into a phosphate buffer solution with pH 7.4 in a concentration of 100 ng/mL, and the resulting solution was mixed with FITC (fluorescein)-labeled anti-cryj-1 antibody solution.

While the microdevice was rotated, the above mixture solution was introduced into the device using a syringe pump to form an antibody-antigen-FITC-labeled antibody complex on the surface of the reaction field A.

After the rotation of the microdevice was stopped, air was sent from the introduction portion 5 shown in FIG. 20, and thereby the mixture solution of the test solution and fluorescent-labeled antibody were discharged from the discharge portion 7. Then, a buffer solution was flowed in the microdevice to wash the inside of the device.

The reaction field A of the microdevice was observed using a fluorescence microscopy.

For comparison, an antigen-FITC modified antibody mixture solution was introduced to the microdevice shown in FIG. 20. The solution itself has such an amount that it can be filled in the reaction field A, and the concentration of the antigen in the solution was adjusted to the same antigen amount as that in the solution prepared in the above case. After reaction for the same time as the above case, the inside of the device was washed with a buffer solution. Then, the reaction field A of the microdevice was observed using a fluorescence microscopy.

As results of these experiments, fluorescence intensity of the reaction field A when the microdevice was rotated was almost five times as that when the microdevice was not rotated.

Thus, according to this Example, even a trace amount of a test substance can be detected with higher sensitivity and for a shorter time than ever before.

Example 2

This Example corresponds to Embodiment 1-6.

As shown in FIG. 12 (a), a reaction field A having a rectangular shape in plan view and a width of 400 μm and a depth of 50 μm was formed on a center-holed (H) main plate 1 having a diameter of 4 cm and a thickness of 1 mm. In addition, an introduction portion 5 and a discharge position 7 were formed at the overlapped area of the reaction field A in the main plate 1 with the lid plate 3 made of a 0.5 mm thick acrylic plate. Then, these were laminated as shown in FIG. 12(b) to complete a microdevice according to this Example.

Albumin aqueous solution was flowed in the microdevice to form an albumin membrane (nonspecific adsorption prevention membrane) on the wall of the reaction field A, and then a buffer solution was flowed for washing, and discharged out of the discharge portion 7.

Cryj-1 was dissolved into a phosphate buffer solution with pH 7.4 in a concentration of 100 ng/mL, and the resulting solution was mixed with FITC (fluorescein)-labeled anti-cryj-1 antibody solution.

While the microdevice was rotated, the above mixture solution was introduced into the device using a syringe pump to form an antibody-antigen-FITC-labeled antibody complex on the surface of the reaction field A.

After the rotation of the microdevice was stopped, air was sent from the introduction portion 5, and thereby the mixture solution of the test solution and fluorescent-labeled antibody were discharged from the discharge portion 7. Then, a buffer solution was flowed in the microdevice to wash the inside of the device.

The reaction field A of the microdevice was observed using a fluorescence microscopy.

For comparison, an antigen-FITC modified antibody mixture solution was introduced to the microdevice described above. The solution itself has such an amount that it can be filled in the reaction field A, and the concentration of the antigen in the solution was adjusted to the same antigen amount as that in the solution prepared in the above case. After reaction for the same time as the above case, the inside of the device was washed with a buffer solution. Then, the reaction field A of the micro device was observed by a fluorescence microscopy.

As results of these experiments, fluorescence intensity of the reaction field A when the microdevice was rotated was almost three times as that when the microdevice was not rotated.

Thus, according to this embodiment, even a trace amount of a test substance can be detected with higher sensitivity and for a shorter time than ever before.

Example 3

This Example Corresponds to Embodiment 4-2. As Shown in FIG. 17(a), a hole H was provided at the center of a turntable 12 with a diameter of 12 cm and a thickness of 1.2 mm. And four recesses with a width of 1.9 cm and a length of 0.5 mm were formed in the turntable.

As shown in FIG. 17(b), a linear reaction field A with a width of 400 μm, a length of 1.5 cm and a depth of 50 μm is formed in a plate with a width of 2 cm, a length of 3 cm and a thick of 1 mm. In addition, a liquid reservoir portion 6 was formed, and then a connection channel C was formed between the liquid reservoir portion and the reaction field A to fabricated a microchip. An anti-cryj-1 antibody was immobilized in the reaction field A of the microchip using a known method.

Albumin aqueous solution was flowed in the microchip to form an albumin membrane (nonspecific adsorption prevention membrane) on the wall of the reaction field A, and then washing was performed with a buffer solution.

Cryj-1 was dissolved into a phosphate buffer solution with pH 7.4 in a concentration of 100 ng/mL, and the resulting solution was mixed with FITC (fluorescein)-labeled anti-cryj-1 antibody.

The above mixture solution was introduced into the microchip using a syringe pump. Then, as shown in FIG. 17 (a), the microchip was positioned and fixed in the turntable 12 so that the following angle was always 45 to 90°: an angle formed between the direction of the centrifugal force generated when the turntable is rotated centered on the center of rotation (a virtual axis located at the center of the hole H) and a tangent line at a part on the wall surface of the reaction field where the greatest centrifugal force is applied. (In this Embodiment, the angle with the tangent line was 90° in the middle of the reaction field A.)

Thereafter, the turntable was rotated to form an antibody-antigen-FITC-labeled antibody complex on the surface of the reaction field A of the microchip.

The rotation of the turntable is stopped, and then air is flowed from the introduction portion 5 to discharge mixture of the test solution and a fluorescent antibody from the discharge portion 7. Then, a buffer solution is flowed in the microchip apparatus to wash the inside of the device.

The reaction field A of the microchip was observed using a fluorescence microscopy.

For comparison, an antigen-FITC modified antibody mixture solution was introduced to the microchip. The solution itself has such an amount that it can be filled in the reaction field A, and the concentration of the antigen in the solution was adjusted to the same antigen amount as that in the solution prepared in the above case. After reaction for the same time as the above case, the inside of the device was washed with a buffer solution. Then, the reaction field A of the microchip was observed using a fluorescence microscopy.

As results of these experiments, fluorescence intensity of the reaction field A when the turntable was rotated was almost three times as that when the turntable was not rotated.

Thus, according to this embodiment, even a trace amount of a test substance can be detected with higher sensitivity and for a shorter time than ever before.

THE AVAILABILITY OF THE INDUSTRY

As described above, according to the invention, there can be provided a microdevice and a microchip apparatus can perform a measurement of the amount of trace samples rapidly and with high sensitive, Thus, the industrial applicability of the present invention is considerable.

DESCRIPTION OF THE CODE

1: Main plate (main component of Rotation board)
2: Detection plate
3: Lid plate
4: Detection portion
5: Introduction portion
6: Liquid reservoir portion
7: Discharge portion
8: Projection (Damming portion)
9: On/off Microvalve
10: On/off Microvalve
11: On/off Microvalve
12: Turntable
20: Immobilized antibody
21: Test substance
22: Test solution
A: Reaction field
B: Connection channel
C: Channel connecting Liquid reservoir portion and Reaction field
D: Channel connecting Introduction portion and Liquid reservoir portion
E: Channel serving as Introduction portion
H: Hole
O: Center of rotation
Q: Center of rotation
100: Microchip
101: Channel
102: Introduction portion
103: Liquid reservoir portion
104: Discharge portion
105: Protein immobilizing portion
110: Microasperity
120: Test substance
121: Labeled substance
122: Antibody
123: Labeled antibody
124: Immune complex
125: Antibody
126: Complex

What is claimed is:

1. A microdevice comprising:
a rotation board configured to rotate about a center of rotation;
a reaction field provided on the rotation board, the reaction field having a farthest wall part from the center of rotation and a center-of-rotation-side wall part located inwardly from the farthest wall part along an imaginary line representing a direction of centrifugal force generated when the rotation board is rotated about the center of rotation; and
an introduction portion for introducing a solution into the reaction field;
a detection portion for detecting an amount of the test substance;
a connection channel for flowing out the solution from the reaction field, wherein the connection channel connects the reaction field and the detection portion; and
a reactant that specifically reacts with a test substance and is immobilized at least on the farthest wall part of the reaction field,
wherein the following angle is always 45 to 90°: an angle formed between the imaginary line and a tangent line that is tangent to the farthest wall part,
the reactant includes at least one selected from the group consisting of: proteins, peptides, amino acids, and imprinted polymers,
the reactant is immobilized to the farthest wall part of the reaction field by physical adsorption, covalent bond of functional groups on the surface of the reaction field with amino groups of the reactant, or an intake of the reactant by a polymer having a three-dimensional network structure, and
the connection channel is positioned farther from the center of rotation of the rotation board than the reaction field and includes an on/off valve.

2. The microdevice according to claim 1, wherein the detection portion is positioned farther from a center of rotation of the rotation board than the reaction field.

3. The microdevice according to claim 2, wherein the connection channel is formed substantially parallel to the direction of the centrifugal force generated with the center of rotation as a starting point.

4. The microdevice according to claim 1, wherein a planar shape of the reaction field provided in the rotation board is a circumference or an arc centered on the center of rotation of the rotation board.

5. The microdevice according to claim 1, wherein a planar shape of the reaction field provided in the rotation board is linear.

6. The microdevice according to claim 1, wherein a liquid reservoir portion for temporarily storing the solution is provided between the introduction portion and the reaction field.

7. The microdevice according to claim 6, wherein an additional on/off valve is provided between the liquid reservoir portion and the reaction field.

8. The microdevice according to claim 1, wherein the rotation board is formed by laminating a group of plates including:

a main plate in which a groove for the reaction field and a groove for the connection channel are formed, and a lid plate in which the introduction portion is formed.

9. The microdevice according to claim 1, wherein the wall of the reaction field is subjected to water repellent treatment.

10. An analytical method using the microdevice according to claim 1, wherein the method comprises:

an introduction step for introducing a solution containing a target substance into the microdevice; and a rotation step of rotating the microdevice, wherein an introduction amount of the solution containing a target substance is less than a volume of the reaction field.

* * * * *